United States Patent

Hirai et al.

[11] Patent Number: 5,523,459
[45] Date of Patent: Jun. 4, 1996

[54] PREPARATION OF α-KETO ACID ESTER

[75] Inventors: Koichi Hirai; Yasuo Nakamura; Kiyotaka Yoshii; Yasunori Fukuda, all of Yamaguchi, Japan

[73] Assignee: Ube Industries, Ltd., Yamaguchi, Japan

[21] Appl. No.: 410,917

[22] Filed: Mar. 27, 1995

[30] Foreign Application Priority Data

Mar. 25, 1994 [JP] Japan .................................. 6-056140
Mar. 25, 1994 [JP] Japan .................................. 6-056141
May 17, 1994 [JP] Japan .................................. 6-102808

[51] Int. Cl.$^6$ ................................................ C07C 69/76
[52] U.S. Cl. ................................................ 560/51; 560/174
[58] Field of Search ........................................ 560/174, 51

[56] References Cited

FOREIGN PATENT DOCUMENTS

| 2809421 | 9/1979 | Germany . |
|---|---|---|
| 2039624 | 3/1977 | Japan . |
| 1097247 | 5/1986 | Japan . |
| 17404 | 1/1993 | Japan . |
| 255190 | 10/1993 | Japan . |
| 56743 | 3/1994 | Japan . |

*Primary Examiner*—Paul J. Killos
*Attorney, Agent, or Firm*—McAulay Fisher Nissen Goldberg & Kiel

[57] ABSTRACT

A process for preparing an α-keto acid ester (oxo acid) of the formula:

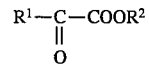

wherein $R^1$ is a hydrogen atom, aliphatic alkyl group of 1–6 carbon atoms, phenyl group or benzyl group, and $R^2$ is an aliphatic alkyl group of 1–6 carbon atoms, which comprises causing an α-hydroxycarboxylic acid ester of the formula:

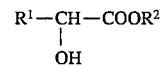

to react with molecular oxygen in a gaseous phase in the presence of copper phosphate, possibly, mounted on a solid carrier.

11 Claims, No Drawings

PREPARATION OF α-KETO ACID ESTER

FIELD OF THE INVENTION

This invention relates to an improvement of a process for the preparation of an α-keto acid ester (oxo acid ester) by reacting an α-hydroxycarboxylic acid ester with molecular oxygen in a gaseous phase.

BACKGROUND OF THE INVENTION

The α-keto acid ester (also referred to as "oxo acid ester") is of value as an intermediate compound for synthesizing a variety of chemical compounds, and particularly for synthesizing α-amino acid. Among the α-keto acid esters, a glyoxylic acid ester prepared from a glycolic acid ester is of great value as a starting compound for preparing a builder of detergent or vanillin or as an intermediate compound for synthesizing pharmaceuticals, agricultural chemicals or polymers.

Heretofore, it has been known that the α-keto acid ester can be prepared by a gaseous catalytic reaction of α-hydroxycarboxylic acid ester with molecular oxygen in the presence of a certain catalyst.

U.S. Pat. No. 4,340,748 discloses the use of a catalyst containing at least one of the elements V, Mo, Ag and Cu, and at least one of the elements Sn, Sb, Bi, elements of the first main group, and elements of the second main group, preferably Sn, Sb, Bi, K, Na, Li, Mg, and Ca, for manufacturing a glyoxylic acid ester (which is one of the α-keto acid ester) by gaseous catalytic reaction of a glycolic acid ester with molecular oxygen. According to our studies, this process is not satisfactory in its productivity, that is, its low rate of production (in terms of space time yield) and its requirement of feed of a large volume of the gas. Further, the Patent suggests that elements of main groups III to V likewise exhibit a catalytic effect. However, no detailed description is given.

Japanese Patent Provisional Publication No. 60(1985)-152442 discloses the use of an expensive silver catalyst for the process of production of glyoxylic acid ester. In the process, the conversion of a glycolic acid ester to a glyoxylic acid ester is ought to be decreased for increasing selectivity to the glyoxylic acid ester. Therefore, the yield of a glyoxylic acid ester is so low as approximately 62% (calculated from about 69% of the conversion of glycolic acid ester and about 89% of the selectivity to glyoxylic acid ester) at the highest.

Japanese Patent Provisional Publication No. 61(1986)-97247 describes a process using a combination of expensive silver and a phosphorus compound (e.g., phosphoric acid, a phosphate such as ammonium dihydrogenphosphate, etc.). The conversion of the glycolic acid ester in this process is as high as 95%. However, the selectivity to the glyoxylic acid ester is as low as about 8%.

The above-mentioned Japanese Patent Provisional Publication No. 61(1986)-97247 further describes a process for the preparation of other α-keto acid esters such as ethyl pyruvate, methyl phenylglyoxylate and methyl phenylpyruvate using a combination of expensive silver and the phosphorus compound. In this process, it may be a problem that the productivity is low owing to a small feed amount of the starting compound, and the expensive silver is used. Further, in this process, the conversions of the above α-hydroxycarboxylic acid esters are 99%, 90% and 92%, respectively, and the selectivities are 80%, 86% and 70%, respectively. Accordingly, the yields of the α-keto acid esters are not satisfactory. Moreover, as described above, it is difficult to obtain the glyoxylic acid ester in a high yield.

Japanese Patent Provisional Publication 2(1990) -91046 describes a process using ferric phosphate supported on an α-alumina carrier as the catalyst. In this process, the yield of a glyoxylic acid ester which is derived from the conversion of glycolic acid ester and the selectivity to glyoxylic acid ester is not sufficiently high. Further, it may be a problem that the feed of gas flow required is large, the preparation of catalyst requires complicated pre-treatment, and the reaction system requires installation of a pre-heating apparatus prior to the reactor.

Bull. Chem. Soc. Jpn., 66, 1542(1993) describes a process for preparing ethyl pyruvate from ethyl lactate using an oxide of Mo, Fe, Sn, Bi, Te, Ti, or Zr. However, the indicated yields of ethyl pyruvate, that is, 80% or less, are not satisfactory.

SUMMARY OF THE INVENTION

The present invention has an object to provide a process for the preparation of an α-keto acid ester including a glyoxylic acid ester by gaseous catalytic reaction between an α-hydroxycarboxylic acid ester and molecular oxygen using an inexpensive catalyst, with a high conversion of the α-hydroxycarboxylic acid ester, a high selectivity (namely, high yield), and a high production rate (in terms of space time yield).

The invention resides in a process for preparing an α-keto acid ester having the formula:

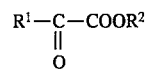

wherein $R^1$ is a substituent selected from those consisting of hydrogen atom, aliphatic alkyl group of 1–6 carbon atoms, phenyl group and benzyl group, and $R^2$ is an aliphatic alkyl group having 1–6 carbon atoms, which comprises causing an α-hydroxycarboxylic acid ester having the formula:

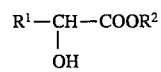

to react with molecular oxygen in a gaseous phase in the presence of copper phosphate.

DETAILED DESCRIPTION OF THE INVENTION

Examples of the α-hydroxycarboxylic acid esters employed in the invention include glycolic acid esters such as methyl glycolate, ethyl glycolate, n-propyl glycolate, isopropyl glycolate, n-butyl glycolate, n-pentyl glycolate, and n-hexyl glycolate; lactic acid esters such as methyl lactate, ethyl lactate, n-propyl lactate, isopropyl lactate, n-butyl lactate, n-pentyl lactate, and n-hexyl lactate; mandelic acid esters such as methyl mandelate, ethyl mandelate, n-propyl mandelate, isopropyl mandelate, n-butyl mandelate, n-pentyl mandelate, and n-hexyl mandelate; and α-hydroxycinnamic acid esters such as methyl α-cinnamate, ethyl α-cinnamate, n-propyl α-cinnamate, isopropyl α-cinnamate, n-butyl α-cinnamate, n-pentyl α-cinnamate, and n-hexyl α-cinnamate.

Examples of the α-keto acid esters of the invention include glyoxylic acid esters such as methyl glyoxylate, ethyl glyoxylate, n-propyl glyoxylate, isopropyl glyoxylate, n-butyl glyoxylate, n-pentyl glyoxylate and n-hexyl glyoxylate; pyruvic acid esters such as methyl pyruvate, ethyl pyruvate, n-propyl pyruvate, isopropyl pyruvate, n-butyl pyruvate, n-pentyl pyruvate, and n-hexyl pyruvate; phenylglyoxylic acid esters such as methyl phenylglyoxylate, ethyl phenylglyoxylate, n-propyl phenylglyoxylate, isopropyl phenylglyoxylate, n-butyl phenylglyoxylate, n-pentyl phenylglyoxylate, and n-hexyl phenylglyoxylate; and phenylpyruvic acid esters such as methyl phenylpyruvate, ethyl phenylpyruvate, n-propyl phenylpyruvate, isopropyl phenylpyruvate, n-butyl phenylpyruvate, n-pentyl phenylpyruvate, and n-hexyl phenylpyruvate.

The molecular oxygen employed in the invention can be generally fed in the form of air. Air or oxygen gas which is diluted with an inert gas such as nitrogen or argon also can be employed. In the latter case, air or oxygen gas is diluted to give a gaseous mixture of an inert gas/oxygen, generally in a molar ratio of 2 to 50, and preferably in a molar ratio of 4 to 30.

The copper phosphate, namely, copper(II) phosphate, employed as catalyst in the invention can be supported on a solid carrier. On the solid carrier, the copper phosphate can be supported in an amount of, generally 1 to 20 weight %, preferably 2 to 15 weight % in terms of the weight of copper atom per the weight of carrier.

Examples of the carriers employable in the invention include silicon carbide, α-alumina, zirconium oxide, titanium oxide, and silica-alumina. Silicon carbide and α-alumina are particularly preferred. Most preferred are silicon carbide of which silica content is less than 30 weight %, particularly less than 25 weight %, and α-alumina. The carrier generally has BET surface area in the range of 0.01 to 20 $m^2/g$, preferably in the range of 0.02 to 10 $m^2/g$. The carrier generally has a mean size of 1 to 20 mm, preferably 1 to 10 mm.

The carrier on which the copper phosphate is supported further can have on its surface metals other than copper in the form of phosphate, oxide, or simple metal. Examples of the other metals include alkali metals such as lithium and potassium; alkaline earth metals such as magnesium or calcium; lanthanide metals such as lanthanum and cerium; molybdenum; tin; manganese; bismuth; cobalt; silver; lead; antimony; and iron. These metals are preferably supported on the carrier in an atomic ratio of less than 2.0 (other metals/copper) singly or in combination.

There is no specific limitation with respect to procedure for placing copper phosphate on a carrier. For instance, the known impregnation method or evaporation-drying method can be employed. In more detail, a salt of copper and optionally a salt of other metal are dissolved in water, and to the solution is added phosphoric acid in a stoichiometric amount. In the resulting solution, the carrier is placed, taken out, dried at about 110° C. in air, and fired at 400°–900° C. in air to obtain the catalyst.

Examples of the salts of copper (other than copper phosphate) and salts of other metals include copper salts such as copper(II) nitrate, copper sulfate, copper(II) chloride; and nitrates, sulfates and chlorides of the following metals: alkali metals lithium and potassium, alkaline earth metal such as magnesium and calcium, lanthanide metals such as lanthanum and cerium, molybdenum, tin, manganese, bismuth, cobalt, silver, lead, antimony and iron. In the case of using one or more metal salts other than the copper phosphate, the metal salt(s) generally is less than two times, preferably less than 1.5 times, as much as the copper phosphate in terms of atomic ratio of the metals.

The copper phosphate can be employed with no carrier. For instance, the copper phosphate can be employed in the form of a powder or molded pieces. There are no specific limitations on their sizes. Preferably, the powder has a mean size of 20 to 100 μm, and the molded pieces have a mean size of 4 to 200 mesh. The copper phosphate can be employed in combination with salts of other metals described above. The copper phosphate with no carrier can be prepared by dispersing copper phosphate, and optionally other metals or salts of other metals such as phosphates and oxides, in water to give a slurry. The slurry is then dried to about 110° C. to give the desired catalyst. Otherwise, an aqueous solution of a copper salt other than copper phosphate and optionally other metal salts, or a slurry prepared by adding water to a copper salt other than copper phosphate or a mixture of such copper salt and a salt or oxide of other metal can be dried to about 110° C. after addition of a stoichiometric amount of phosphoric acid. These methods per se are already known. The catalyst is prepared by optionally pulverizing the dried product, molding into pellets, and firing thus processed products in air at 300° to 900° C. The obtained powder or pellets are employed as catalyst generally after adjusting their sizes within the abovementioned ranges.

According to the invention, the α-hydroxycarboxylic acid ester and the molecular oxygen can be subjected to gaseous catalytic reaction under the following reaction conditions to give the α-keto acid ester. The gaseous catalytic reaction is generally performed in a reactor containing the catalyst at a temperature of 150° to 400° C., preferably 200° to 350° C. and at a pressure of 1 (atmospheric pressure) to 5 $kg/cm^2$. In more detail, the α-hydroxycarboxylic acid ester is fed into the reactor in an amount of 0.2–6.0 g/hr (preferably 0.3–3.0 g/hr) per 1 g of the catalyst, and the molecular oxygen is fed in an amount of 0.5–30 ml/min. (preferably 1–15 ml/min.) per 1 g of the catalyst. The molar ratio of the oxygen to the α-hydroxycarboxylic acid ester generally is 0.3 to 5, preferably 0.5 to 3, more preferably 0.5 to 2 (oxygen/α-hydroxycarboxylic acid ester).

There are no specific limitations with respect to the reactor, so long as the reactor can allow the reaction under passage of gases. The catalyst can be placed in the known fixed bed, fluidized bed, and boiled bed. Preferred is the fixed bed.

The α-hydroxycarboxylic acid ester can be fed with an inert solvent such as alcohol, water, acetonitrile, toluene, or cyclohexane to increase the selectivity of the desired α-keto acid ester. The weight ratio of the solvent to the α-hydroxycarboxylic acid ester generally is less than 10, preferably 0.02–10, and more preferably 0.04–8(solvent/α-hydroxycarboxylic acid ester). In the case of using the copper phosphate catalyst with no carrier, the weight ratio of the solvent to α-hydroxycarboxylic acid ester generally is less than 1, preferably 0.02–0.8, more preferably 0.04–0.6 (solvent/α-hydroxycarboxylic acid ester). Examples of the alcohols include aliphatic lower alcohols having 1–6 carbon atoms such as methanol, ethanol, n-propanol, isopropanol, n-butanol, n-pentanol, and n-hexanol. Most preferred are methanol and ethanol.

In the process of the invention, the α-keto acid ester are recovered together with unreacted α-hydroxycarboxylic acid ester and by-produced water. The desired α-keto acid ester can be separated and purified by known methods such as distillation.

The present invention is further described in more detail by the following examples. In the following examples, STY (space time yield; g/l.hr) of α-keto acid ester, conversion (%) of α-hydroxycarboxylic acid ester, selectivity (%) to α-keto acid ester, and yield (%) of α-keto acid ester are obtained by the following formulas wherein KE and HE mean α-keto acid ester and α-hydroxycarboxylic acid ester, respectively:

$$\text{STY of KE (g/l·hr)} = \frac{\text{Amount of produced KE (g)}}{\text{Catalyst (l)} \times \text{Reaction period (hr)}}$$

$$\text{Conversion of HE (\%)} = \frac{\text{Reacted amount of HE (mol)}}{\text{Feed amount of HE (mol)}} \times 100$$

$$\text{Selectivity to KE (\%)} = \frac{\text{Produced amount of KE (mol)}}{\text{Reacted amount of HE (mol)}} \times 100$$

Yield of KE (%) = Conversion of HE (%) × Selectivity to KE (%)

Remarks: KE: α-keto acid ester
HE: α-hydroxycarboxylic acid ester

EXAMPLE 1

Preparation of catalyst

In a catalyst preparation solution prepared by dissolving 2.44 g (10.0 mmol) of copper(II) nitrate trihydrate [Cu(NO$_3$)$_2$.3H$_2$O] and 0.77 g of 85% phosphoric acid (6.68 mmol) in 3 ml of water was placed 11.2 g of silicon carbide (mean particle size: 3 mm, BET surface area: less than 1 m$^2$/g, silica content: 11 wt. %, available from Fujimi Co., Ltd. under the product number of TL-S51) for 30 minutes for impregnation of silicon carbide with copper phosphate. The silicon carbide was taken out of the solution and placed under vacuum at 40° C. for removing water. Thus impregnated silicon carbide was dried in air at 110° C. for 12 hours. The dried silicon carbide was fired twice, namely, at 400° C. for 3 hours, and 800° C. for 3 hours, to give the desired catalyst. X-ray fluorescence analysis indicated that the copper phosphate was supported on the silicon carbide (carrier) in an amount of 5.3 wt. % (in terms of copper atom amount).

Preparation of methyl glyoxylate

In a glass reactor tube (inner diameter: 9 mm) were successively charged 8 ml of the above-obtained catalyst and 14 g of glass beads. The reactor was installed vertically in an electric furnace, and the electric furnace was controlled to maintain the temperature in the catalyst layer as given in Table 1. From the upper part of the reactor, a methyl glycolate solution comprising methanol and methyl glycolate (1:1, weight ratio) was fed into the reactor at a rate of 11.6 g/hr. At the same time, air and nitrogen gas were fed in the form of their mixture at rates of 200 ml/min. and 94 ml/min., respectively. Thus, a gaseous catalytic reaction was carried out for one hour at the temperature set forth in Table 1 and at atmospheric pressure. The products were passed through the reactor and then collected in an ice-chilled trap.

The reaction products collected in the trap were analyzed by gas chromatography. It was found that the STY of methyl glyoxylate was 565 g/l.hr, the conversion of methyl glycolate was 89.6%, the selectivity of methyl glyoxylate was 88.9%, and the yield of methyl glyoxylate was 80.0%.

EXAMPLE 2

Preparation of catalyst

The procedures of Example 1 were repeated except for employing a catalyst preparation solution prepared by dissolving 2.44 g (10.0 mmol) of copper(II) nitrate trihydrate [Cu(NO$_3$)$_2$.3H$_2$O], 0.81 g (2.0 mmol) of iron(II) nitrate nonahydrate [Fe(NO$_3$)$_3$.9H$_2$O], and 1.05 g of 85% phosphoric acid (9.1 mmol) in 3 ml of water, to prepare a catalyst.

The analysis of the catalyst indicated that Cu in the form of its phosphate was supported on the carrier in an amount of 5.1 wt. % and Fe/Cu was 0.2 (atomic ratio).

Preparation of methyl glyoxylate

The procedures of Example 1 were repeated except for employing the above-obtained catalyst (8 ml) to carry out the gaseous catalytic reaction. The results are set forth in Table 1.

EXAMPLE 3

Preparation of catalyst

The procedures of Example 1 were repeated except for employing a catalyst preparation solution prepared by dissolving 2.44 g (10.0 mmol) of copper(II) nitrate trihydrate [Cu(NO$_3$)$_2$.3H$_2$O], 2.03 g (5.0 mmol) of iron(II) nitrate nonahydrate [Fe(NO$_3$)$_3$.9H$_2$O], and 1.36 g of 85% phosphoric acid (11.8 mmol) in 3 ml of water, to prepare a catalyst.

The analysis of the catalyst indicated that Cu in the form of its phosphate was supported on the carrier in an amount of 4.9 wt. % and Fe/Cu was 0.5 (atomic ratio).

Preparation of methyl glyoxylate

The procedures of Example 1 were repeated except for employing the above-obtained catalyst (8 ml) to carry out the gaseous catalytic reaction. The results are set forth in Table 1.

EXAMPLE 4

Preparation of catalyst

The procedures of Example 1 were repeated except for employing a catalyst preparation solution prepared by dissolving 2.44 g (10.0 mmol) of copper(II) nitrate trihydrate [Cu(NO$_3$)$_2$.3H$_2$O], 2.71 g (6.7 mmol) of iron(II) nitrate nonahydrate [Fe(NO$_3$)$_3$.9H$_2$O], and 1.56 g of 85% phosphoric acid (13.5 mmol) in 3 ml of water, to prepare a catalyst.

The analysis of the catalyst indicated that Cu in the form of its phosphate was supported on the carrier in an amount of 4.8 wt. % and Fe/Cu was 0.67 (atomic ratio).

Preparation of methyl glyoxylate

The procedures of Example 1 were repeated except for employing the above-obtained catalyst (8 ml) and changing the air feed rate into 80 ml/min. to carry out the gaseous catalytic reaction. The results are set forth in Table 1.

EXAMPLE 5

Preparation of catalyst

The procedures of Example 1 were repeated except for employing a catalyst preparation solution prepared by dissolving 2.44 g (10.0 mmol) of copper(II) nitrate trihydrate [Cu(NO$_3$)$_2$.3H$_2$O], 4.04 g (10.0 mmol) of iron(II) nitrate nonahydrate [Fe(NO$_3$)$_3$.9H$_2$O], and 1.95 g of 85% phosphoric acid (16.9 mmol) in 3 ml of water, to prepare a catalyst.

The analysis of the catalyst indicated that Cu in the form of its phosphate was supported on the carrier in an amount of 4.7 wt. % and Fe/Cu was 1.0 (atomic ratio).

Preparation of methyl glyoxylate

The procedures of Example 1 were repeated except for employing the above-obtained catalyst (8 ml) to carry out the gaseous catalytic reaction. The results are set forth in Table 1.

EXAMPLE 6

Preparation of catalyst

The procedures of Example 1 were repeated except for employing a catalyst preparation solution prepared by dissolving 2.44 g (10.0 mmol) of copper(II) nitrate trihydrate $[Cu(NO_3)_2.3H_2O]$, 5.37 g (13.3 mmol) of iron(II) nitrate nonahydrate $[Fe(NO_3)_3.9H_2O]$, and 2.34 g of 85% phosphoric acid (20 mmol) in 3 ml of water, to prepare a catalyst.

The analysis of the catalyst indicated that Cu in the form of its phosphate was supported on the carrier in an amount of 4.5 wt. % and Fe/Cu was 1.33 (atomic ratio).

Preparation of methyl glyoxylate

The procedures of Example 1 were repeated except for employing the above-obtained catalyst (8 ml) to carry out the gaseous catalytic reaction. The results are set forth in Table 1.

COMPARISON EXAMPLE 1

Preparation of catalyst

The procedures of Example 1 were repeated except for employing a catalyst preparation solution prepared by dissolving 4.04 g (10.0 mmol) of iron(II) nitrate nonahydrate $[Fe(NO_3)_3.9H_2O]$ and 1.21 g of 85% phosphoric acid (10.5 mmol) in 3 ml of water, to prepare a catalyst.

The analysis of the catalyst indicated that Fe in the form of its phosphate was supported on the carrier in an amount of 4.5 wt. %.

Preparation of methyl glyoxylate

The procedures of Example 1 were repeated except for employing the above-obtained catalyst (8 ml) to carry out the gaseous catalytic reaction. The results are set forth in Table 1.

EXAMPLE 7

Preparation of catalyst

The procedures of Example 1 were repeated except for employing a catalyst preparation solution prepared by dissolving 2.44 g (10.0 mmol) of copper(II) nitrate trihydrate $[Cu(NO_3)_2.3H_2O]$, 4.04 g (10.0 mmol) of lanthanum nitrate hexahydrate $[La(NO_3)_3.6H_2O]$, and 1.05 g of 85% phosphoric acid (9.1 mmol) in 3 ml of water, to prepare a catalyst.

The analysis of the catalyst indicated that Cu in the form of its phosphate was supported on the carrier in an amount of 5.1 wt. % and La/Cu was 0.2 (atomic ratio).

Preparation of methyl glyoxylate

The procedures of Example 1 were repeated except for employing the above-obtained catalyst (8 ml) to carry out the gaseous catalytic reaction. The results are set forth in Table 1.

EXAMPLE 8

Preparation of catalyst

The procedures of Example 4 were repeated to prepare a catalyst.

The analysis of the catalyst indicated that Cu in the form of its phosphate was supported on the carrier in an amount of 4.8 wt. % and Fe/Cu was 0.67 (atomic ratio).

Preparation of methyl glyoxylate

The procedures of Example 1 were repeated except for employing the above-obtained catalyst (8 ml), changing the air feed rate into 80 ml/min., and employing an aqueous methyl glycolate solution (water: methyl glycolate= 9:95, by weight) at a feed rate of 6.1 g/hr., to carry out the gaseous catalytic reaction. The results are set forth in Table 1.

EXAMPLE 9

Preparation of catalyst

The procedures of Example 5 were repeated to prepare a catalyst.

The analysis of the catalyst indicated that Cu in the form of its phosphate was supported on the carrier in an amount of 4.7 wt. % and Fe/Cu was 1.0 (atomic ratio).

Preparation of methyl glyoxylate

The procedures of Example 8 were repeated except for employing the above-obtained catalyst (8 ml), to carry out the gaseous catalytic reaction. The results are set forth in Table 1.

TABLE 1

| | | Reaction Conditions | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 1 | 305 | 11.6 | 1 | 200 | 89.6 | 88.9 | 80.0 | 565 |
| Ex. 2 | 305 | 11.6 | 1 | 200 | 92.0 | 90.3 | 83.1 | 589 |
| Ex. 3 | 285 | 11.6 | 1 | 200 | 87.0 | 91.0 | 79.2 | 561 |
| Ex. 4 | 284 | 11.6 | 1 | 80 | 94.4 | 96.6 | 91.2 | 646 |
| Ex. 5 | 307 | 11.6 | 1 | 200 | 86.3 | 92.4 | 79.7 | 565 |
| Ex. 6 | 305 | 11.6 | 1 | 200 | 88.5 | 98.0 | 86.7 | 615 |

TABLE 1-continued

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| CE. 1 | 293 | 11.6 | 1 | 200 | 50.7 | 79.9 | 40.5 | 287 |
| Ex. 7 | 305 | 11.6 | 1 | 200 | 89.4 | 90.1 | 80.5 | 571 |
| Ex. 8 | 283 | 6.1 | 5/95 | 80 | 97.2 | 92.0 | 89.4 | 662 |
| Ex. 9 | 307 | 6.1 | 5/95 | 200 | 89.4 | 85.4 | 76.3 | 566 |

Remarks:
CE: Comparison Example
MG: Methyl glycolate
MGO: Methyl glyoxylate
Sol: Solvent (methanol for Examples 1–7 and Comparison Example 1, and water for Examples 8 & 9)

EXAMPLE 10

Preparation of catalyst

The procedures of Example 1 were repeated to prepare a catalyst.

The analysis of the catalyst indicated that Cu in the form of its phosphate was supported on the carrier in an amount of 5.3 wt. %.

Preparation of methyl glyoxylate

The procedures of Example 1 were repeated except for employing the above-obtained catalyst (8 ml) and feeding methyl glycolate (5.8 g/hr.) per se in place of the methyl glycolate solution, to carry out the gaseous catalytic reaction. The results are set forth in Table 2.

COMPARISON EXAMPLE 2

Preparation of catalyst

The procedures of Example 1 were repeated except for employing a catalyst preparation solution prepared by dissolving 2.44 g (10.0 mmol) of copper(II) nitrate trihydrate [$Cu(NO_3)_2 \cdot 3H_2O$] in 3 ml of water, to prepare a catalyst.

The X-ray diffraction analysis of the catalyst indicated that copper in the form of copper(II) oxide was supported on the carrier in an amount of 4.8 wt. %.

Preparation of methyl glyoxylate

The procedures of Example 1 were repeated except for employing the above-obtained catalyst (8 ml) to carry out the gaseous catalytic reaction. The results are set forth in Table 2.

EXAMPLE 11

Preparation of catalyst

The procedures of Example 2 were repeated to prepare a catalyst.

The analysis of the catalyst indicated that Cu in the form of its phosphate was supported on the carrier in an amount of 5.1 wt. %, and Fe/Cu was 0.2 (atomic ratio).

Preparation of methyl glyoxylate

The procedures of Example 10 were repeated except for employing the above-obtained catalyst (8 ml), to carry out the gaseous catalytic reaction. The results are set forth in Table 2.

EXAMPLE 12

Preparation of catalyst

The procedures of Example 3 were repeated to prepare a catalyst.

The analysis of the catalyst indicated that Cu in the form of its phosphate was supported on the carrier in an amount of 4.9 wt. %, and Fe/Cu was 0.5 (atomic ratio).

Preparation of methyl glyoxylate

The procedures of Example 10 were repeated except for employing the above-obtained catalyst (8 ml), to carry out the gaseous catalytic reaction. The results are set forth in Table 2.

EXAMPLE 13

Preparation of catalyst

The procedures of Example 4 were repeated to prepare a catalyst.

The analysis of the catalyst indicated that Cu in the form of its phosphate was supported on the carrier in an amount of 4.8 wt. %, and Fe/Cu was 0.67 (atomic ratio).

Preparation of methyl glyoxylate

The procedures of Example 10 were repeated except for employing the above-obtained catalyst (8 ml) and changing the air feed rate into 80 ml/min. to carry out the gaseous catalytic reaction. The results are set forth in Table 2.

EXAMPLE 14

Preparation of catalyst

The procedures of Example 5 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 10 were repeated except for employing the above-obtained catalyst (8 ml), to carry out the gaseous catalytic reaction. The results are set forth in Table 2.

EXAMPLE 15

Preparation of catalyst

The procedures of Example 6 were repeated to prepare a catalyst.

The analysis of the catalyst indicated that Cu in the form of its phosphate was supported on the carrier in an amount of 4.5 wt. %, and Fe/Cu was 1.33 (atomic ratio).

Preparation of methyl glyoxylate

The procedures of Example 10 were repeated except for employing the above-obtained catalyst (8 ml), to carry out the gaseous catalytic reaction. The results are set forth in Table 2.

COMPARISON EXAMPLE 3

Preparation of catalyst

The procedures of Comparison Example 1 were repeated to prepare a catalyst.

The analysis of the catalyst indicated that Fe in the form of its phosphate was supported on the carrier in an amount of 4.5 wt. %.

Preparation of methyl glyoxylate

The procedures of Example 10 were repeated except for employing the above-obtained catalyst (8 ml), to carry out the gaseous catalytic reaction. The results are set forth in Table 2.

EXAMPLE 16

Preparation of catalyst

The procedures of Example 7 were repeated to prepare a catalyst.

The analysis of the catalyst indicated that Cu in the form of its phosphate was supported on the carrier in an amount of 5.1 wt. %, and La/Cu was 0.2 (atomic ratio).

Preparation of methyl glyoxylate

The procedures of Example 10 were repeated except for employing the above-obtained catalyst (8 ml), to carry out the gaseous catalytic reaction. The results are set forth in Table 2.

EXAMPLE 17

Preparation of catalyst

The procedures of Example 5 were repeated except for using 11.2 g of silicon carbide (mean particle size: 4 mm, BET surface area: less than 1 $m^2/g$, silica content: 0.5 wt. %, available from Tokai Konetsu Co., Ltd. under the product number of TSS-99175) as carrier, to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 1 were repeated except for employing the above-obtained catalyst (8 ml) and changing the air feed rate into 80 ml/min., to carry out the gaseous catalytic reaction. The results are set forth in Table 3.

EXAMPLE 18

Preparation of catalyst

The procedures of Example 17 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 17 were repeated except for employing the above-obtained catalyst (8 ml) and feeding methyl glycolate (5.8 g/hr.) per se in place of the methyl glycolate solution, to carry out the gaseous catalytic reaction. The results are set forth in Table 3.

COMPARISON EXAMPLE 4

Preparation of catalyst

The procedures of Example 17 were repeated except for employing a catalyst preparation solution prepared by dissolving 4.04 g (10.0 mmol) of iron(II) nitrate nonahydrate [$Fe(NO_3)_3 \cdot 9H_2O$] and 1.21 g of 85% phosphoric acid (10.5 mmol) in 3 ml of water, to prepare a catalyst.

TABLE 2

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 10 | 305 | 5.8 | 0 | 200 | 90.5 | 76.7 | 69.4 | 492 |
| CE. 2 | 335 | 5.8 | 0 | 200 | 78.5 | 2.4 | 1.9 | 13 |
| Ex. 11 | 305 | 5.8 | 0 | 200 | 97.3 | 77.6 | 75.5 | 535 |
| Ex. 12 | 285 | 5.8 | 0 | 200 | 92.4 | 77.5 | 71.6 | 508 |
| Ex. 13 | 283 | 5.8 | 0 | 80 | 95.1 | 86.0 | 81.8 | 580 |
| Ex. 14 | 307 | 5.8 | 0 | 200 | 89.0 | 80.0 | 71.2 | 505 |
| Ex. 15 | 304 | 5.8 | 0 | 200 | 84.6 | 87.6 | 74.1 | 525 |
| CE. 3 | 305 | 5.8 | 0 | 200 | 73.3 | 57.7 | 42.3 | 300 |
| Ex. 16 | 305 | 5.8 | 0 | 200 | 96.1 | 77.1 | 74.1 | 525 |

Remarks:
CE: Comparison Example
MG: Methyl glycolate
MGO: Methyl glyoxylate

The analysis of the catalyst indicated that Fe in the form of its phosphate was supported on the carrier in an amount of 4.5 wt. %.

Preparation of methyl glyoxylate

The procedures of Example 17 were repeated except for employing the above-obtained catalyst (8 ml), changing the air feed rate into 200 ml/min., and feeding methyl glycolate (5.8 g/hr.) per se in place of the methyl glycolate solution, to carry out the gaseous catalytic tion. The results are set forth in Table 3.

EXAMPLE 19

Preparation of catalyst

The procedures of Example 5 were repeated except for using 11.2 g of silicon carbide (mean particle size: 4 mm, BET surface area: less than 1 $m^2/g$, silica content: 7.5 wt. %, available from Tokai Konetsu Co., Ltd. under the product number of TSS-90306) as carrier, to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 17 were repeated except for employing the above-obtained catalyst (8 ml) and changing the air feed rate into 160 ml/min., to carry out the gaseous catalytic reaction. The results are set forth in Table 3.

EXAMPLE 20

Preparation of catalyst

The procedures of Example 19 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 19 were repeated except for employing the above-obtained catalyst (8 ml) and a methyl glycolate solution comprising acetonitrile and methyl glycolate ( 1:1, by weight ), to carry out the gaseous catalytic reaction. The results are set forth in Table 3.

EXAMPLE 21

Preparation of catalyst

The procedures of Example 19 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 19 were repeated except for employing the above-obtained catalyst (8 ml), changing the air feed rate into 80 ml/min., and feeding methyl glycolate (5.8 g/hr.) per se in place of the methyl glycolate solution, to carry out the gaseous catalytic reaction. The results are set forth in Table 3.

COMPARISON EXAMPLE 5

Preparation of catalyst

The procedures of Example 19 were repeated except for employing a catalyst preparation solution prepared by dissolving 4.04 g (10.0 mmol) of iron(II) nitrate nonahydrate $[Fe(NO_3)_3 \cdot 9H_2O]$ and 1.21 g of 85% phosphoric acid (10.5 mmol) in 3 ml of water, to prepare a catalyst.

The analysis of the catalyst indicated that Fe in the form of its phosphate was supported on the carrier in an amount of 4.5 wt. %.

Preparation of methyl glyoxylate

The procedures of Example 17 were repeated except for employing the above-obtained catalyst (8 ml), changing the air feed rate into 200 l/min., and feeding methyl glycolate (5.8 g/hr.) per se in place of the methyl glycolate solution, to carry out the gaseous catalytic reaction. The results are set forth in Table 3.

TABLE 3

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 17 | 280 | 11.6 | 1 | 80 | 86.0 | 92.4 | 79.5 | 563 |
| Ex. 18 | 275 | 5.8 | 0 | 80 | 94.0 | 81.3 | 76.4 | 542 |
| CE. 4 | 305 | 5.8 | 0 | 200 | 36.5 | 72.3 | 26.4 | 187 |
| Ex. 19 | 269 | 11.6 | 1 | 160 | 96.8 | 99.4 | 96.2 | 682 |
| Ex. 20 | 277 | 11.6 | 1 | 160 | 96.3 | 91.6 | 88.2 | 625 |
| Ex. 21 | 277 | 5.8 | 0 | 80 | 93.9 | 93.1 | 87.4 | 620 |
| CE. 5 | 306 | 5.8 | 0 | 200 | 90.4 | 56.2 | 50.8 | 360 |

Remarks:
CE: Comparison Example
MG: Methyl glycolate
MGO: Methyl glyoxylate
Sol: Solvent (methanol for Examples 17 & 19, and acetonitrile for Example 20)

EXAMPLE 22

Preparation of catalyst

The procedures of Example 5 were repeated except for using 11.2 g of α-alumina (mean particle size: 3 mm, BET surface area: less than 1 $m^2/g$, silica content: 13 wt. %, available from Fujimi Co., Ltd. under the product number of AL-S73) as carrier, to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 1 were repeated except for employing the above-obtained catalyst (8 ml) and feeding a methyl glycolate solution comprising methanol and methyl glycolate (3:7, by weight) at a feed rate of 8.3 g/hr., to carry out the gaseous catalytic reaction. The results are set forth in Table 4.

EXAMPLE 23

Preparation of catalyst

The procedures of Example 22 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 22 were repeated except for employing the above-obtained catalyst (8 ml), and feeding methyl glycolate (5.8 g/hr.) per se in place of the methyl glycolate solution, to carry out the gaseous catalytic reaction. The results are set forth in Table 4.

COMPARISON EXAMPLE 6

Preparation of catalyst

The procedures of Example 22 were repeated except for employing a catalyst preparation solution prepared by dissolving 4.04 g (10.0 mmol) of iron(II) nitrate nonahydrate [$Fe(NO_3)_3 \cdot 9H_2O$] and 1.21 g of 85% phosphoric acid (10.5 mmol) in 3 ml of water, to prepare a catalyst.

The analysis of the catalyst indicated that Fe in the form of its phosphate was supported on the carrier in an amount of 4.5 wt. %.

Preparation of methyl glyoxylate

The procedures of Example 22 were repeated except for employing the above-obtained catalyst (8 ml), and feeding methyl glycolate (5.8 g/hr.) per se in place of the methyl glycolate solution, to carry out the gaseous catalytic reaction. The results are set forth in Table 4.

EXAMPLE 24

Preparation of catalyst

The procedures of Example 5 were repeated except for using α-alumina (mean particle size: 4.7 mm, BET surface area: less than 0.05 m$^2$/g, silica content: 12 wt. %, available from Norton Co., Ltd. under the product number of SA-5205) as carrier, to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 22 were repeated except for employing the above-obtained catalyst (8 ml), to carry out the gaseous catalytic reaction. The results are set forth in Table 4.

EXAMPLE 25

Preparation of catalyst

The procedures of Example 24 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl glyoxylate

The procedures of Example 22 were repeated except for employing the above-obtained catalyst (8 ml), and feeding methyl glycolate (5.8 g/hr.) per se in place of the methyl glycolate solution, to carry out the gaseous catalytic reaction. The results are set forth in Table 4.

COMPARISON EXAMPLE 7

Preparation of catalyst

The procedures of Example 24 were repeated except for employing a catalyst preparation solution prepared by dissolving 4.04 g (10.0 mmol) of iron(II) nitrate nonahydrate [$Fe(NO_3)_3 \cdot 9H_2O$] and 1.21 g of 85% phosphoric acid (10.5 mmol) in 3 ml of water, to prepare a catalyst.

The analysis of the catalyst indicated that Fe in the form of its phosphate was supported on the carrier in an amount of 4.5 wt. %.

Preparation of methyl glyoxylate

The procedures of Example 22 were repeated except for employing the above-obtained catalyst (8 ml), and feeding methyl glycolate (5.8 g/hr.) per se in place of the methyl glycolate solution, to carry out the gaseous catalytic reaction. The results are set forth in Table 4.

TABLE 4

| | Reaction Conditions | | | | Reaction Results | | | |
| --- | --- | --- | --- | --- | --- | --- | --- | --- |
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 22 | 278 | 8.3 | 3/7 | 200 | 95.8 | 95.3 | 91.3 | 648 |
| Ex. 23 | 280 | 5.8 | 0 | 200 | 94.6 | 89.2 | 84.4 | 598 |

TABLE 4-continued

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| CE. 6 | 305 | 5.8 | 0 | 200 | 89.2 | 64.9 | 57.9 | 410 |
| Ex. 24 | 280 | 8.3 | 3/7 | 200 | 85.5 | 96.5 | 82.5 | 586 |
| Ex. 25 | 280 | 5.8 | 0 | 200 | 95.2 | 89.3 | 85.0 | 603 |
| CE. 7 | 302 | 5.8 | 0 | 200 | 72.4 | 70.5 | 51.0 | 362 |

Remarks:
CE: Comparison Example
MG: Methyl glycolate
MGO: Methyl glyoxylate
Sol: Solvent (methanol for Examples 22 & 24)

EXAMPLE 26

Preparation of catalyst

The procedures of Example 19 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl pyruvate

The procedures of Example 1 were repeated except for employing the above-obtained catalyst (8 ml), feeding air and nitrogen at feed rates of 90 ml/min. and 180 ml/min., respectively, and feeding a methyl lactate solution comprising methanol and methyl lactate ( 5:1, by weight) at a feed rate of 15.6 g/hr., to carry out the gaseous catalytic reaction. There was obtained methyl pyruvate as α-keto acid ester. The results are set forth in Table 5.

EXAMPLE 27

Preparation of catalyst

The procedures of Example 19 were repeated except for employing a catalyst preparation solution prepared by dissolving 3.66 g (15.0 mmol) of copper(II) nitrate trihydrate [Cu(NO$_3$)$_2$.3H$_2$O], 4.04 g (10.0 mmol) of iron(II) nitrate hexahydrate [Fe(NO$_3$)$_3$.6H$_2$O], and 2.33 g of 85% phosphoric acid (20.2 mmol) in 4 ml of water, to prepare a catalyst.

The analysis of the catalyst indicated that Cu in the form of its phosphate was supported on the carrier in an amount of 7.0 wt. % and Fe/Cu was 0.67 (atomic ratio).

Preparation of methyl pyruvate

The procedures of Example 26 were repeated except for employing the above-obtained catalyst (8 ml) to carry out the gaseous catalytic reaction. There was obtained methyl pyruvate as α-keto acid ester. The results are set forth in Table 5.

EXAMPLE 28

Preparation of catalyst

The procedures of Example 19 were repeated except for using α-alumina (mean particle size: 4.7 mm, BET surface area: less than 0.05 m$^2$/g silica content: 11.8 wt. %, available from Norton Co., Ltd. under the product number of SA-50205) as carrier, to prepare a catalyst.

The analysis of the catalyst indicated that Cu in the form of its phosphate was supported on the carrier in an amount of 4.7 wt. %, and Fe/Cu was 0.67 (atomic ratio).

Preparation of methyl pyruvate

The procedures of Example 26 were repeated except for employing the above-obtained catalyst (8 ml), to carry out the gaseous catalytic reaction. There was obtained methyl pyruvate as α-keto acid ester. The results are set forth in Table 5.

COMPARISON EXAMPLE 8

Preparation of catalyst

The procedures of Comparison Example 5 were repeated to prepare a catalyst.

The analysis of the catalyst indicated that Fe in the form of its phosphate was supported on the carrier in an amount of 4.5 wt. %.

Preparation of methyl pyruvate

The procedures of Example 26 were repeated except for employing the above-obtained catalyst (8 ml), to carry out the gaseous catalytic reaction. There was obtained methyl pyruvate as α-keto acid ester. The results are set forth in Table 5.

EXAMPLE 29

Preparation of catalyst

The procedures of Example 19 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl phenylglyoxylate

The procedures of Example 1 were repeated except for employing the above-obtained catalyst (8 ml), feeding air and nitrogen at feed rates of 35 ml/min. and 70 ml/min., respectively, and feeding a methyl mandelate solution comprising methanol and methyl mandelate (6:1, by weight) at a feed rate of 17.0 g/hr., to carry out the gaseous catalytic reaction. There was obtained methyl phenylglyoxylate as α-keto acid ester. The results are set forth in Table 5.

EXAMPLE 30

Preparation of catalyst

The procedures of Example 29 were repeated to prepare a catalyst.

The analysis of the catalyst indicated that Cu in the form of its phosphate was supported on the carrier in an amount of 4.7 wt. %, and Fe/Cu was 1.0 (atomic ratio).

Preparation of methyl phenylglyoxylate

The procedures of Example 29 were repeated except for employing the above-obtained catalyst (8 ml), feeding air at a feed rate of 56 ml/min, and feeding the methyl mandelate solution at a feed rate of 30.7 g/hr., to carry out the gaseous catalytic reaction. There was obtained methyl phenylglyoxylate as α-keto acid ester. The results are set forth in Table 5.

EXAMPLE 31

Preparation of catalyst

The procedures of Example 28 were repeated to prepare a catalyst.

The analysis of the catalyst indicated that Cu in the form of its phosphate was supported on the carrier in an amount of 7.0 wt. %, and Fe/Cu was 0.67 (atomic ratio).

Preparation of methyl phenylglyoxylate

The procedures of Example 29 were repeated except for employing the above-obtained catalyst (8 ml), feeding air at a feed rate of 56 ml/min, to carry out the gaseous catalytic reaction. There was obtained methyl phenylglyoxylate as α-keto acid ester. The results are set forth in Table 5.

Preparation of methyl glyoxylate

In a glass reactor tube (inner diameter: 9 mm) were successively charged 8 ml of the above-obtained catalyst and 20 ml of glass beads. The reactor was installed vertically in an electric furnace, and the electric furnace was controlled to maintain the temperature in the catalyst layer as given in Table 6. From the upper part of the reactor, a methyl glycolate solution comprising methanol and methyl glycolate (3:7, weight ratio) was fed into the reactor at a rate of 8.4 g/hr. At the same time, air and nitrogen gas were fed in the form of their mixture at rates of 79 ml/min. and 187 ml/min., respectively. Thus, a gaseous catalytic reaction was carried out for one hour at the temperature set forth in Table 6, and at atmospheric pressure. The products were passed through the reactor and then collected in an ice-chilled trap.

The reaction products collected in the trap were analyzed by gas chromatography. It was found that the STY of methyl glyoxylate was 576 g/l.hr, the conversion of methyl glycolate was 90.9%, the selectivity of methyl glyoxylate was 89.0%, and the yield of methyl glyoxylate was 80.1%.

EXAMPLE 33

Preparation of catalyst

The procedures of Example 32 were repeated except for employing a catalyst preparation solution prepared by adding 14.5 g (33.3 mmol) of copper phosphate trihydrate [$Cu_3(PO_4)_2 \cdot 3H_2O$] and 6.7 g (33 mmol) of iron(II) phosphate tetrahydrate [$FePO_4 \cdot 4H_2O$] to 30 ml of water, to prepare a catalyst.

X-ray fluorescence analysis indicated that an atomic ratio of iron to Cu (catalyst) was 0.3 (Fe/Cu).

TABLE 5

| | Reaction Conditions | | | | Reaction Results | | | |
|---|---|---|---|---|---|---|---|---|
| | Temp. (°C.) | Feed (HE) (g/hr) | Sol/HE (wt) | Feed (Air) (ml/min) | Conv (HE) (%) | Sel (KA) (%) | Yield (KA) (%) | STY (KA) (g/l · hr) |
| Ex. 26 | 330 | 15.6 | 5 | 90 | 93.1 | 90.9 | 84.6 | 270 |
| Ex. 27 | 330 | 15.6 | 5 | 90 | 96.5 | 93.3 | 90.0 | 287 |
| Ex. 28 | 330 | 15.6 | 5 | 90 | 90.9 | 89.9 | 81.7 | 260 |
| CE. 8 | 320 | 15.6 | 5 | 90 | 75.5 | 66.3 | 50.1 | 160 |
| Ex. 29 | 280 | 17.0 | 6 | 35 | 96.2 | 94.9 | 91.3 | 274 |
| Ex. 30 | 280 | 30.7 | 6 | 56 | 90.1 | 94.8 | 85.4 | 463 |
| Ex. 31 | 280 | 17.0 | 6 | 35 | 98.7 | 96.9 | 95.6 | 287 |

Remarks:
CE: Comparison Example
HE: Methyl α-hydroxycarboxylate (methyl lactate for Examples 26–28 and Comparison Example 8, and methyl mandelate for Examples 29–31)
KA: Methyl glyoxylate (methyl pyruvate for Examples 26–28 and Comparison Example 8, and methyl phenylglyoxylate for Examples 29–31)
Sol: Solvent (methanol for Examples 26–31 and Comparison Example 8)

EXAMPLE 32

Preparation of catalyst

A catalyst preparation solution prepared by adding 43.5 g (100 mmol) of copper phosphate trihydrate [$Cu_3(PO_4)_2 \cdot 3H_2O$] to 30 ml of water was kneaded, crushed and squeezed for 30 min., and then dried in air at 110° C. for 12 hrs. The dried product was pulverized into a powder and molded into pellets having a diameter of 5 mm. The pellets were fired at 450° C. for 5 hrs, and pulverized into pieces of 1 to 2 mm. Thus, the desired catalyst was prepared.

Preparation of methyl glyoxylate

The procedures of Example 32 were repeated except for employing the above-obtained catalyst (8 ml) to carry out the gaseous catalytic reaction. The results are set forth in Table 6.

EXAMPLE 34

Preparation of catalyst

The procedures of Example 32 were repeated except for employing a catalyst preparation solution prepared by adding 14.5 g (33.3 mmol) of copper phosphate trihydrate [Cu$_3$(PO$_4$)$_2$.3H$_2$O] and 13.4 g (60 mmol) of iron(II) phosphate tetrahydrate [FePO$_4$.4H$_2$O] to 30 ml of water, to prepare a catalyst.

The analysis indicated that an atomic ratio of iron to Cu (catalyst) was 0.6 (Fe/Cu).

Preparation of methyl glyoxylate

The procedures of Example 32 were repeated except for employing the above-obtained catalyst (8 ml) and feeding a methyl glycolate solution comprising methanol and methyl glycolate (1:1, by weight), to carry out the gaseous catalytic reaction. The results are set forth in Table 6.

EXAMPLE 35

Preparation of catalyst

The procedures of Example 32 were repeated except for employing a catalyst preparation solution prepared by adding 14.5 g (33.3 mmol) of copper phosphate trihydrate [Cu(PO$_4$)$_2$.3H$_2$O] and 22.3 g (100 mmol) of iron(II) phosphate tetrahydrate [FePO$_4$.4H$_2$O] to 30 ml of water, to prepare a catalyst.

The analysis indicated that an atomic ratio of iron to Cu (catalyst) was 1.0 (Fe/Cu).

Preparation of methyl glyoxylate

The procedures of Example 32 were repeated except for employing the above-obtained catalyst (8 ml) to carry out the gaseous catalytic reaction. The results are set forth in Table 6.

EXAMPLE 36

Preparation of catalyst

The procedures of Example 32 were repeated except for employing a catalyst preparation solution prepared by adding 8.7 g (20 mmol) of copper phosphate trihydrate [CU$_3$(PO$_4$)$_2$.3H$_2$O] and 22.3 g (100 mmol) of iron(II) phosphate tetrahydrate [FePO$_4$.4H$_2$O] to 30 ml of water, to prepare a catalyst.

The analysis indicated that an atomic ratio of iron to Cu (catalyst) was 1.7 (Fe/Cu).

Preparation of methyl glyoxylate

The procedures of Example 32 were repeated except for employing the above-obtained catalyst (8 ml) to carry out the gaseous catalytic reaction. The results are set forth in Table 6.

COMPARISON EXAMPLE 9

Preparation of catalyst

The procedures of Example 32 were repeated except for employing a catalyst preparation solution prepared by adding 44.6 g (200 mmol) of iron(II) phosphate tetrahydrate [FePO$_4$.4H$_2$O] to 30 ml of water, to prepare a catalyst.

Preparation of methyl glyoxylate

The procedures of Example 32 were repeated except for employing the above-obtained catalyst (8 ml) to carry out the gaseous catalytic reaction. The results are set forth in Table 6.

TABLE 6

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 32 | 305 | 8.4 | 3/7 | 79 | 90.0 | 89.0 | 80.1 | 576 |
| Ex. 33 | 305 | 8.4 | 3/7 | 79 | 91.3 | 85.8 | 78.3 | 563 |
| Ex. 34 | 305 | 11.9 | 1 | 79 | 92.5 | 90.9 | 84.1 | 612 |
| Ex. 35 | 303 | 8.4 | 3/7 | 79 | 95.1 | 93.2 | 88.6 | 637 |
| Ex. 36 | 303 | 8.4 | 3/7 | 79 | 90.6 | 74.1 | 67.1 | 482 |
| CE. 9 | 305 | 8.4 | 3/7 | 79 | 61.3 | 85.0 | 52.1 | 374 |

Remarks:
CE: Comparison Example
MG: Methyl glycolate
MGO: Methyl glyoxylate
Sol: Solvent (methanol)

EXAMPLE 37

Preparation of catalyst

The procedures of Example 32 were repeated to prepare a catalyst.

Preparation of methyl glyoxylate

The procedures of Example 32 were repeated except for employing the above-obtained catalyst (8 ml), and feeding methyl glycolate (6.0 g/hr.) per se in place of the methyl glycolate solution, to carry out the gaseous catalytic reaction. The results are set forth in Table 7.

EXAMPLE 38

Preparation of catalyst

The procedures of Example 33 were repeated to prepare a catalyst.

The analysis indicated that an atomic ratio of iron to Cu (catalyst) was 0.3 (Fe/Cu).

Preparation of methyl glyoxylate

The procedures of Example 37 were repeated except for employing the above-obtained catalyst (8 ml) to carry out the gaseous catalytic reaction. The results are set forth in Table 7.

EXAMPLE 39

Preparation of catalyst

The procedures of Example 34 were repeated to prepare a catalyst.

The analysis indicated that an atomic ratio of iron to Cu (catalyst) was 0.6 (Fe/Cu).

Preparation of methyl glyoxylate

The procedures of Example 37 were repeated except for employing the above-obtained catalyst (8 ml) to carry out the gaseous catalytic reaction. The results are set forth in Table 7.

EXAMPLE 40

Preparation of catalyst

The procedures of Example 35 were repeated to prepare a catalyst.

The analysis indicated that an atomic ratio of iron to Cu (catalyst)was 1.0 (Fe/Cu).

Preparation of methyl glyoxylate

The procedures of Example 37 were repeated except for employing the above-obtained catalyst (8 ml) to carry out the gaseous catalytic reaction. The results are set forth in Table 7.

EXAMPLE 41

Preparation of catalyst

The procedures of Example 36 were repeated to prepare a catalyst.

The analysis indicated that an atomic ratio of iron to Cu (catalyst) was 1.7 (Fe/Cu).

Preparation of methyl glyoxylate

The procedures of Example 37 were repeated except for employing the above-obtained catalyst (8 ml) to carry out the gaseous catalytic reaction. The results are set forth in Table 7.

COMPARISON EXAMPLE 10

Preparation of catalyst

The procedures of Comparison Example 9 were repeated to prepare a catalyst.

Preparation of methyl glyoxylate

The procedures of Example 37 were repeated except for employing the above-obtained catalyst (8 ml) to carry out the gaseous catalytic reaction. The results are set forth in Table 7.

EXAMPLE 42

Preparation of catalyst

The procedures of Example 32 were repeated except for employing a catalyst preparation solution prepared by dissolving 24.2 g (100 mmol) of copper nitrate trihydrate $[Cu(NO_3)_2.3H_2O]$ and 12.1 g (30 mmol) of iron(II) nitrate nonahydrate $[Fe(NO_3)_3.9H_2O]$ in a mixture of 10 ml of water and 11.2 g of 85% phosphoric acid (97 mmol) under heating, to prepare a catalyst.

The analysis indicated that an atomic ratio of iron to Cu (catalyst) was 0.3 (Fe/Cu).

Preparation of methyl glyoxylate

The procedures of Example 37 were repeated except for employing the above-obtained catalyst (8 ml) to carry out the gaseous catalytic reaction. The results are set forth in Table 7.

EXAMPLE 43

Preparation of catalyst

The procedures of Example 32 were repeated except for employing a catalyst preparation solution prepared by adding 14.5 g (33.3 mmol) of copper phosphate trihydrate $[Cu(PO_4)_2.3H_2O]$ and 1.71 g (3.34 mmol) of cobalt (II) phosphate octahydrate $[Co_3(PO_4)_2.8H_2O]$ to 30 ml of water, to prepare a catalyst.

The analysis indicated that an atomic ratio of cobalt to Cu (catalyst) was 0.1 (Co/Cu).

Preparation of methyl glyoxylate

The procedures of Example 37 were repeated except for employing the above-obtained catalyst (8 ml) to carry out the gaseous catalytic reaction. The results are set forth in Table 7.

EXAMPLE 44

Preparation of catalyst

The procedures of Example 32 were repeated except for employing a catalyst preparation solution prepared by adding 14.5 g (33.3 mmol) of copper phosphate trihydrate $[Cu_3(PO_4)_2.3H_2O]$ and 1.49 g (3.35 mmol) of manganese(II) phosphate pentahydrate $[Mn_3(PO_4)_2.5H_2O]$ to 30 ml of water, to prepare a catalyst.

The analysis indicated that an atomic ratio of manganese to Cu (catalyst) was 0.1 (Mn/Cu).

Preparation of methyl glyoxylate

The procedures of Example 37 were repeated except for employing the above-obtained catalyst (8 ml) to carry out the gaseous catalytic reaction. The results are set forth in Table 7.

TABLE 7

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 37 | 304 | 6.0 | 0 | 79 | 92.5 | 76.9 | 71.1 | 521 |
| Ex. 38 | 295 | 6.0 | 0 | 79 | 95.1 | 76.7 | 72.9 | 535 |
| Ex. 39 | 305 | 6.0 | 0 | 79 | 96.1 | 80.3 | 77.2 | 566 |
| Ex. 40 | 305 | 6.0 | 0 | 79 | 97.1 | 85.3 | 82.8 | 607 |
| Ex. 41 | 290 | 6.0 | 0 | 79 | 96.9 | 67.5 | 65.4 | 480 |
| CE. 10 | 305 | 6.0 | 0 | 79 | 65.2 | 64.4 | 42.0 | 308 |
| Ex. 42 | 304 | 6.0 | 0 | 79 | 98.5 | 86.3 | 85.0 | 623 |
| Ex. 43 | 305 | 6.0 | 0 | 79 | 92.3 | 77.8 | 71.8 | 600 |
| Ex. 44 | 291 | 6.0 | 0 | 79 | 95.2 | 78.8 | 75.0 | 580 |

Remarks:
CE: Comparison Example
MG: Methyl glycolate
MGO: Methyl glyoxylate
Sol: Solvent

EXAMPLE 45

Preparation of catalyst

The procedures of Example 33 were repeated to prepare a catalyst.

The analysis indicated that an atomic ratio of iron to Ca (catalyst) was 0.3 (Fe/Cu).

Preparation of methyl glyoxylate

The procedures of Example 37 were repeated except for employing the above-obtained catalyst (8 ml), and feeding methyl glycolate (6.7 g/hr.) per se in place of the methyl glycolate solution, to carry out the gaseous catalytic reaction. The results are set forth in Table 8.

COMPARISON EXAMPLE 11

Preparation of catalyst

The procedures of Comparison Example 9 were repeated to prepare a catalyst,

Preparation of methyl glyoxylate

The procedures of Example 45 were repeated except for employing the above-obtained catalyst (8 ml) to carry out the gaseous catalytic reaction, The results are set forth in Table 8.

TABLE 8

| | Reaction Conditions | | | | Reaction Results | | | |
|---|---|---|---|---|---|---|---|---|
| | Temp. (°C.) | Feed (MG) (g/hr) | Sol/MG (wt) | Feed (Air) (ml/min) | Conv (MG) (%) | Sel (GO) (%) | Yield (MGO) (%) | STY (MGO) (g/l · hr) |
| Ex. 45 | 295 | 6.7 | 0 | 79 | 91.3 | 75.1 | 68.6 | 562 |
| CE. 11 | 295 | 6.7 | 0 | 79 | 66.2 | 60.4 | 40.0 | 328 |

Remarks:
CE: Comparison Example
MG: Methyl glycolate
MGO: Methyl glyoxylate
Sol: Solvent

We claim:

1. A process for preparing an α-keto acid ester having the formula:

$$R^1-\underset{\underset{O}{\|}}{C}-COOR^2$$

wherein $R^1$ is a substituent selected from those consisting of hydrogen atom, aliphatic alkyl group of 1–6 carbon atoms, phenyl group and benzyl group, and $R^2$ is an aliphatic alkyl group having 1–6 carbon atoms, which comprises reacting an α-hydroxycarboxylic acid ester having the formula:

$$R^1-\underset{\underset{OH}{|}}{CH}-COOR^2$$

with molecular oxygen in a gaseous phase in the presence of copper phosphate.

2. The process of claim 1, wherein the copper phosphate is supported on a solid carrier.

3. The process of claim 1, wherein the α-keto acid ester is an alkyl glyoxylate and the α-hydroxycarboxylic acid ester is an alkyl glycolate.

4. The process of claim 1, wherein the α-keto acid ester is an alkyl pyruvate and the α-hydroxycarboxylic acid ester is an alkyl lactate.

5. The process of claim 1, wherein the α-keto acid ester is an alkyl phenyl glyoxylate and the α-hydroxycarboxylic acid ester is an alkyl mandelate.

6. The process of claim 1, wherein the α-keto acid ester is an alkyl phenylpyruvate and the α-hydroxycarboxylic acid ester is an alkyl hydroxycinnamate.

7. The process of claim 1, wherein the molecular oxygen is supplied in the form of air.

8. The process of claim 1, wherein the copper phosphate is supported on a solid carrier in an amount of 1–30 weight % in terms of copper atom of the phosphate per the carrier.

9. The process of claim 1, wherein the copper phosphate is supported on a solid carrier selected from the group consisting of carbon nitride, α-alumina, zirconium oxide, titanium dioxide, and silica-alumina.

10. The process of claim 1, wherein the copper phosphate is supported on a solid carrier having a particle size of 1 to 20 mm and a BET specific surface of 0.01 to 20 $m^2/g$.

11. The process of claim 1, wherein the reaction is performed at a temperature of 150° to 400° C. and at a pressure of 1 to 5 $kg/cm^2$.

* * * * *